United States Patent
Freas et al.

(10) Patent No.: US 7,328,057 B2
(45) Date of Patent: Feb. 5, 2008

(54) SHUNT PASSER OR LIKE SURGICAL INSTRUMENT CONFIGURED FOR RECEIVING DIFFERENT-SIZED POSITIONING LOCATORS OF IMAGE-GUIDED SURGICAL SYSTEM

(75) Inventors: Mark Freas, Melbourne, FL (US); Thomas L. Bridges, Melbourne, FL (US)

(73) Assignee: Medtronic, Inc., Minneapolis, MN (US)

( * ) Notice: Subject to any disclaimer, the term of this patent is extended or adjusted under 35 U.S.C. 154(b) by 695 days.

(21) Appl. No.: 10/360,539

(22) Filed: Feb. 6, 2003

(65) Prior Publication Data
US 2004/0158259 A1 Aug. 12, 2004

(51) Int. Cl.
*A61B 5/05* (2006.01)
(52) U.S. Cl. ........................... 600/424; 606/108
(58) Field of Classification Search .................. 606/53, 606/56, 59, 80, 96, 108, 129, 130; 604/164, 604/272, 264; 600/424–427, 566, 567
See application file for complete search history.

(56) References Cited

U.S. PATENT DOCUMENTS

| | | | | | |
|---|---|---|---|---|---|
| 3,406,685 | A | * | 10/1968 | May ..................... | 604/164.11 |
| 4,781,691 | A | * | 11/1988 | Gross .................... | 604/164.06 |
| 5,469,853 | A | * | 11/1995 | Law et al. .............. | 600/463 |
| 5,505,698 | A | * | 4/1996 | Booth et al. ........... | 604/103.11 |
| 5,993,463 | A | * | 11/1999 | Truwit ................... | 606/130 |
| 6,197,003 | B1 | | 3/2001 | Howard, III et al. ... | 604/164.12 |
| 6,298,262 | B1 | | 10/2001 | Franck et al. .......... | 600/426 |

* cited by examiner

*Primary Examiner*—Michael J. Hayes
*Assistant Examiner*—Victor Nguyen
(74) *Attorney, Agent, or Firm*—Scott A. Marks

(57) ABSTRACT

This document discusses, among other things, examples of a shunt passer or like surgical instrument configured for receiving different-sized positioning locators of an image guided surgical system. In one example, the surgical instrument includes portions having different diameters for receiving the different-sized affixation mechanisms for the positioning locators.

13 Claims, 1 Drawing Sheet

SHUNT PASSER OR LIKE SURGICAL INSTRUMENT CONFIGURED FOR RECEIVING DIFFERENT-SIZED POSITIONING LOCATORS OF IMAGE-GUIDED SURGICAL SYSTEM

FIELD OF THE INVENTION

This document relates generally to instruments for use in image-guided surgery, and more specifically, but not by way of limitation, to a shunt passer or like surgical instrument that is configured for receiving different-sized positioning locators of an image-guided surgical system.

BACKGROUND

Image guided surgery (IGS) typically uses preoperative patient images to guide a subsequent surgical procedure. The preoperative patient images are displayed on computerized IGS workstation. A surgical instrument is remotely tracked by an optical or other positioning system that is coupled to the IGS workstation. This permits an image of the instrument and/or its trajectory path to be displayed on the preoperative patient images, which, in turn, helps the surgeon plan the entry point and trajectory to a desired target location within the patient. In one example, the light emitting diodes (LEDs) or passive reflectors are attached to the surgical instrument. The optical positioning system includes a camera that can detect light from such locators to determine the position and orientation of the surgical instrument. Among other things, the present inventor has recognized an unmet need for providing surgical instruments that work with a variety of IGS workstation optical positioning systems and components. This increases the convenience and lowers the cost of the IGS procedure.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
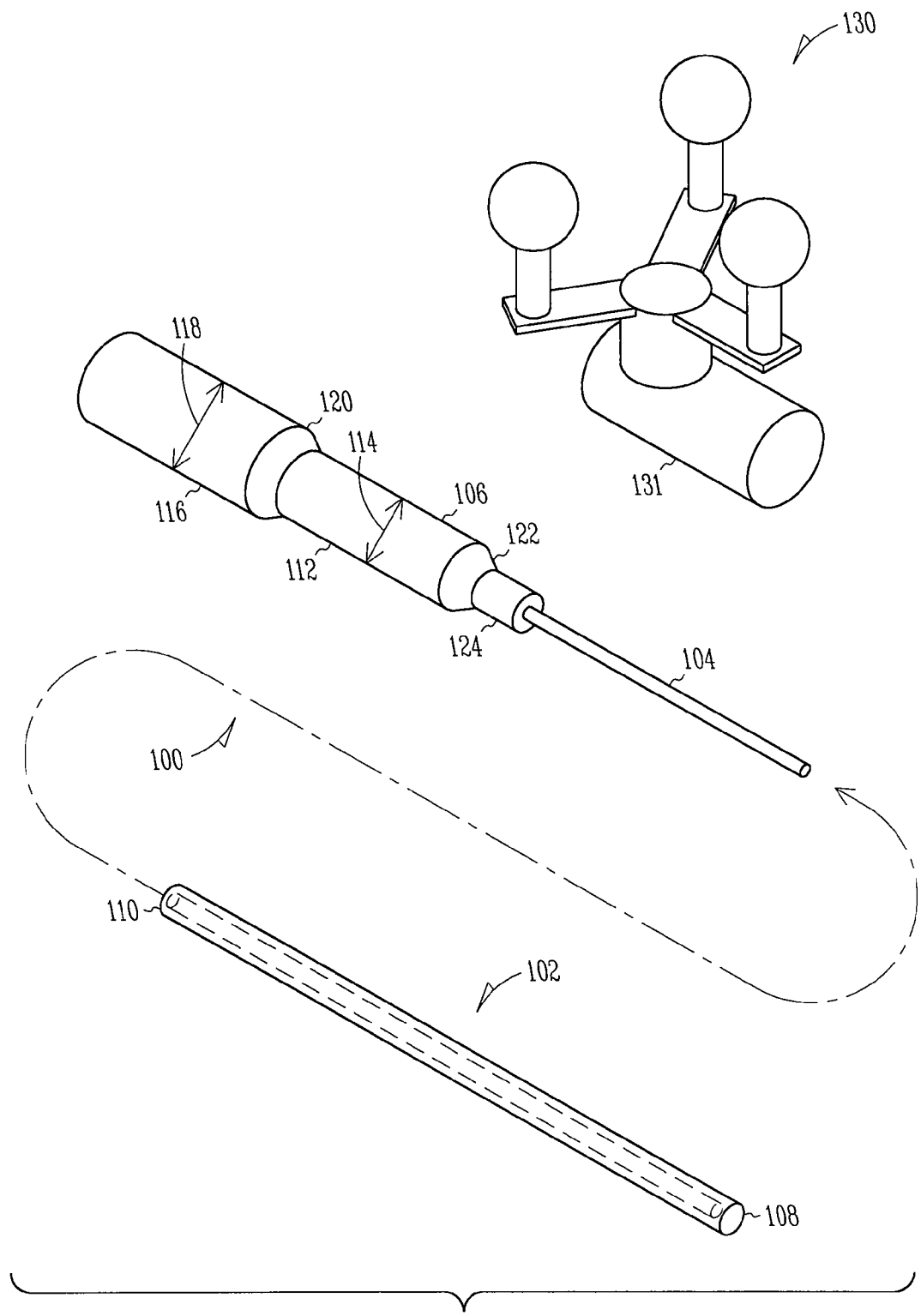
FIG. 1 is a schematic diagram illustrating generally, by way of example, but not by way of limitation, a shunt passer and an associated shunt catheter.

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

FIG. 1 is a schematic diagram illustrating generally, by way of example, but not by way of limitation, a shunt passer 100 and an associated shunt catheter 102. In this example, the shunt passer 100 includes a stainless steel or other distal stylet portion 104 (or other elongated minimally-invasive primary instrument portion) and a plastic or other proximal hub portion 106 that is molded or otherwise attached thereto. The solid stylet 104 is sized and shaped to allow the hollow tubular shunt catheter 102 to be slid over the stylet 104. This permits the stylet 104 and the catheter 102 to be introduced into a subject's brain, or into some other region of interest in a human, an animal, or an inanimate object. The stylet 104 provides rigidity and torsional stability to the catheter 102 while it is being introduced. This permits the catheter 102 to be more easily and accurately guided toward the desired target.

In one example, the stylet 104 and the catheter 102 are sized and shaped to permit them to be introduced through a lumen of a fixed or adjustable orientation trajectory guide device. The trajectory guide device may be mounted directly to a subject's skull or affixed to equipment located in close proximity thereto. Some suitable examples of trajectory guide devices are described in: Skakoon et al. U.S. patent application Ser. No. 09/828,451 entitled "DEEP ORGAN ACCESS DEVICE AND METHOD," which was filed on Apr. 6, 2001; Matthew Solar's U.S. patent application Ser. No. 10/325615 entitled "ORGAN ACCESS DEVICE AND METHOD," which was filed on Dec. 20, 2002; Truwit U.S. Pat. No. 5,993,463; and Truwit U.S. Pat. No. 6,267,769; each of which is incorporated by reference herein in its entirety, including its description of trajectory guide structures and methods for introducing an instrument and guiding the instrument toward the target.

However, the surgical instrument need not be introduced through a trajectory guide. In an alternative example, the surgical instrument is sized and shaped to permit it to be introduced through a burr hole (which is typically between about 8 millimeters and about 14 millimeters in diameter) or other minimally invasive opening in a subject's skull. In this document, the term "minimally-invasive" refers to techniques that are less invasive than conventional surgery; the term "minimally-invasive" is not intended to be restricted to the least-invasive technique possible.

In this example, a distal end 108 of the catheter 102 is closed and a proximal end 110 of the catheter 102 is open. In one example, the shunt passer 100 is used to introduce the catheter 102 into a ventricular system (or elsewhere) in a brain, such as for providing drainage and/or introducing a medicament. In one such example, the catheter 102 includes one or more holes on its cylindrical circumferential outer surface at or near its distal end 108. Such holes provide fluid communication between the hollow interior tube of the catheter 102 and the external environment in which the distal end 108 of the catheter 102 is disposed. In one example, the stylet 104 has a cylindrical outer diameter of about 0.038 inches, and is about 6 inches in length between the hub 106 and the distal end of the stylet 104.

In FIG. 1, the hub 106 includes a distal cylindrical portion 112 having a first diameter 114. The hub 106 also includes a proximal cylindrical portion 116 having a second diameter 118 that is different from (in this example, larger than) the first diameter 114 of the distal cylindrical portion 112. In this example, the hub 106 also includes a tapered portion 120 between the distal cylindrical portion 112 and the proximal cylindrical portion 116. In this example, the hub 106 also includes a tapered portion 122 between the distal cylindrical portion 112 and a head 124 portion of the hub 106, which is affixed to a proximal portion of the stylet 104. The illustrated configuration, in which the distal cylindrical portion is of a smaller diameter than the proximal cylindrical portion, is easier to mold than would be the case if the diameters were reversed.

In the example of FIG. 1, the different diameters 112 and 116 of the respective different portions of the hub 106 permit easy affixation of an IGS locating device 130 using a clamp 131 thereto, wherein the affixed locating device permits a camera or other remote detector in an IGS remote positioning system to detect the position and orientation of the shunt passer 100. This permits the IGS workstation to display the position and orientation of the shunt passer 100 with the preoperative images on the IGS workstation, which, in turn, assists the surgeon in planning and or performing the surgical procedure for guiding the shunt passer 100 toward the desired target. In one example, an IGS locating device includes "hose clamps" or other affixation devices that are tailored toward being affixed only to a particular diameter cylindrical surgical device, and are not well-suited to being affixed to a cylindrical surgical device of a different diameter.

In one illustrative example, a suitable IGS workstation is commercially available as the STEALTHSTATION, sold by Medtronic, Inc., of Minneapolis, Minn. In this example, the STEALTHSTATION includes the SURETRAK locating device, which is capable of being affixed to a surgical instrument. The SURETRAK locating device includes LEDs that are remotely detectable by a camera of the optical positioning system of the STEALTHSTATION. The STEALTHSTATION comes with different sized clamps for the SURETRAK locating devices, each of which is adapted for being affixed to different diameter surgical instruments. For example, Part No. 960-564 are SURETRAK locating device affixation bands (similar to hose-clamps) that are designed to be affixed to an instrument that is ⅜" in diameter. In another example, Part No. 960-565 are SURETRAK locating device affixation bands (again, similar to hose-clamps) that are designed to be affixed to an instrument that is ½" in diameter. Thus, to use such a locating device in conjunction with a surgical instrument, a surgeon would ordinarily have to be sure to have on hand a locating device having the properly sized affixation bands. However, the multiple diameters 114 (e.g., ⅜") and 118 (e.g., ½") of the hub 106 of the shunt passer 100 avoid such complexity. Instead, the shunt passer 100 allows either a ⅜" or a ½" SURETRAK locating device to be affixed thereto, by affixing the band to a like diameter portion of the hub 106. Thus, the shunt passer 100 reduces the complexity and cost of the surgical procedure.

In another illustrative example, an IGS workstation is commercially available as the VECTORVISION, sold by BrainLAB, Inc., having a U.S. office in Westchester, Ill. In this example, the VECTORVISION includes the STARLINK locating device, which is capable of being affixed to a surgical instrument. The STARLINK locating device includes reflective spheres that are remotely detectable by a camera of the optical positioning system of the VECTORVISION. The VECTORVISION comes with separate sized (Small, Medium, Large, and Extra Large) clamps for the STARLINK locating devices, each of which is adapted for being affixed to a different diameter surgical instrument. Thus, to use such a locating device in conjunction with a surgical instrument, a surgeon would ordinarily have to be sure to have on hand a locating device having the properly sized affixation bands. In one example, the hub 106 includes four different diameter portions, respectively sized to receive each of the respective Small, Medium, Large, and Extra Large clamps (similar to the two different diameter portions illustrated in FIG. 1) In this sense, FIG. 1 is merely illustrative; the shunt passer 100 may include any number of portions providing any number of different diameters for accommodating various sized clamps or other affixation devices of IGS locating devices from the same or different manufacturers. Moreover, although FIG. 1 illustrates such affixation (by way of illustrative example, but not by way of limitation) to a shunt passer, it is understood that, in other embodiments, the multi-diameter affixation portion is included in other types of surgical instruments capable of being used in an IGS surgical procedure. Examples of other types of IGS instruments include, without limitation neuroendoscopes, biopsy needles, sensing or stimulation electrodes, and burr hole drills.

It is to be understood that the above description is intended to be illustrative, and not restrictive. For example, the above-described embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

What is claimed is:

1. An apparatus comprising:
   an elongate primary instrument, including proximal and distal ends that is sized and shaped for receiving a shunt catheter thereupon for introducing the elongate primary instrument and shunt catheter together into a brain;
   a hub, coupled to the proximal end of the elongate primary instrument, the hub specifically sized and shaped to accept differently-sized affixation devices of a locator device of a remote positioning system, in which the hub comprises:
      a first cylindrical portion, including a first outer diameter that is specifically sized and shaped to accept a first sized affixation device of a first locator device of a remote positioning system; and
      a second cylindrical portion, coupled to the first cylindrical portion, the second cylindrical portion including a second outer diameter that is different from the first outer diameter, the second outer diameter being specifically sized and shaped to accept a different second sized affixation device of a second locator device of the remote positioning system; and
   at least one of the first locator device or the second locator device including at least one clamp that is specifically sized and shaped for circumferentially encompassing one of the first and second outer diameters of the respective first and second cylindrical portions;
   wherein at least one of the first locator device or the second locator device permits detection by a remote locating system, to determine a position and orientation of the elongate primary instrument.

2. The apparatus of claim 1, in which the first outer diameter is about ⅜ inches and the second outer diameter is about ½ inches.

3. The apparatus of claim 1, in which the first cylindrical portion is more distal than the second cylindrical portion, and in which the first outer diameter is smaller than the second outer diameter.

4. The apparatus of claim 1, further comprising a shunt catheter, sized and shaped for being received over the primary instrument.

5. The apparatus of claim 1, in which the primary instrument is sized and shaped to permit the primary instrument to be introduced through a trajectory guide to a target.

6. apparatus of claim 1, in which the primary instrument is sized and shaped to permit the primary instrument to be introduced through a burr hole to a target.

7. The apparatus of claim 1, in which the primary instrument is sized and shaped to permit the primary instrument to be introduced using minimally-invasive surgery.

8. A shunt passer comprising:
an elongate solid cylindrical stylet, sized and shaped to be introduced through a trajectory guide to a target, the stylet including proximal and distal ends;
a hub, coupled to the proximal end of the stylet, the hub specifically sized and shaped to accept differently-sized affixation devices of a locator device of a remote positioning system of an image-guided workstation, and in which the hub comprises:
a first cylindrical portion, including a first outer diameter that is specifically sized and shaped to accept a first sized affixation device of a first locator device; and
a second cylindrical portion, coupled to the first cylindrical portion, the second cylindrical portion including a second outer diameter that is different from the first outer diameter, the second outer diameter being specifically sized and shaped to accept a different second sized affixation device of a different second locator device; and
at least one of the first locator device or the second locator device including at least one clamp that is specifically sized and shaped for circumferentially encompassing one of the first and second outer diameters of the respective first and second cylindrical portions;
wherein at least one of the first locator device or the second locator device permits detection by a remote locating system, to determine a position and orientation of the elongate solid cylindrical stylet.

9. The apparatus of claim 8, in which the first cylindrical portion is coupled to the proximal end of the stylet, and in which the second cylindrical portion is more proximal than the first cylindrical portion, and in which the first outer diameter is smaller than the second outer diameter.

10. The apparatus of claim 9, in which the first outer diameter is about ⅜ inches and the second outer diameter is about ½ inches.

11. An apparatus comprising:
an elongate solid cylindrical stylet, sized and shaped to be introduced through a trajectory guide to a target, the stylet including proximal and distal ends;
a hub, coupled to the proximal end of the stylet, in which the hub comprises:
a first non-faceted cylindrical circumferential portion, including a first outer diameter that is specifically sized and shaped to accept a first sized affixation device of a first locator device; and
a second non-faceted cylindrical circumferential portion, coupled to the first cylindrical portion, the second cylindrical portion including a second outer diameter that is different from the first outer diameter, the second outer diameter being specifically sized and shaped to accept a different second sized affixation device of a different second locator device; and
at least one of the first locator device or the second locator device including at least one clamp that is specifically sized and shaped for circumferentially encompassing one of the first and second outer diameters of the respective first and second cylindrical portions;
wherein at least one of the first locator device or the second locator device permits detection by a remote locating system, to determine a position and orientation of the elongate solid cylindrical stylet.

12. The apparatus of claim 11, in which the first cylindrical portion is coupled to the proximal end of the stylet, and in which the second cylindrical portion is more proximal than the first cylindrical portion, and in which the first outer diameter is smaller than the second outer diameter.

13. The apparatus of claim 11, in which the first outer diameter is about ⅜ inches and the second outer diameter is about ½ inches.

* * * * *